United States Patent [19]

Kuris et al.

[11] 4,193,197

[45] Mar. 18, 1980

[54] FLUID SUPPLY UNIT AND SYSTEMS FOR DENTAL AND MEDICAL INSTRUMENTS

[75] Inventors: Arthur Kuris, Riverdale; Leonard W. Suroff, Jericho, both of N.Y.

[73] Assignee: Aquasonic Products Corp., New York, N.Y.

[21] Appl. No.: 843,416

[22] Filed: Oct. 19, 1977

Related U.S. Application Data

[63] Continuation-in-part of Ser. No. 702,536, Jul. 6, 1976, abandoned.

[51] Int. Cl.² .............................................. A61C 13/00
[52] U.S. Cl. ...................................................... 433/82
[58] Field of Search ...................................... 32/22, 28

[56] References Cited

U.S. PATENT DOCUMENTS

| 3,094,780 | 6/1963 | Maurer et al. | 32/28 |
| 3,505,737 | 4/1970 | Merolla | 32/28 |

*Primary Examiner*—Robert Peshock
*Attorney, Agent, or Firm*—Leonard W. Suroff

[57] ABSTRACT

An auxiliary enclosed fluid supply unit or system that is adapted to be used in conjunction with commercially available professional dental and medical equipment to permit the user to select a variety of fluids to be administered to the patient during dental and other procedures and maintain desired levels of sterility in the operative cite of the patient.

31 Claims, 13 Drawing Figures

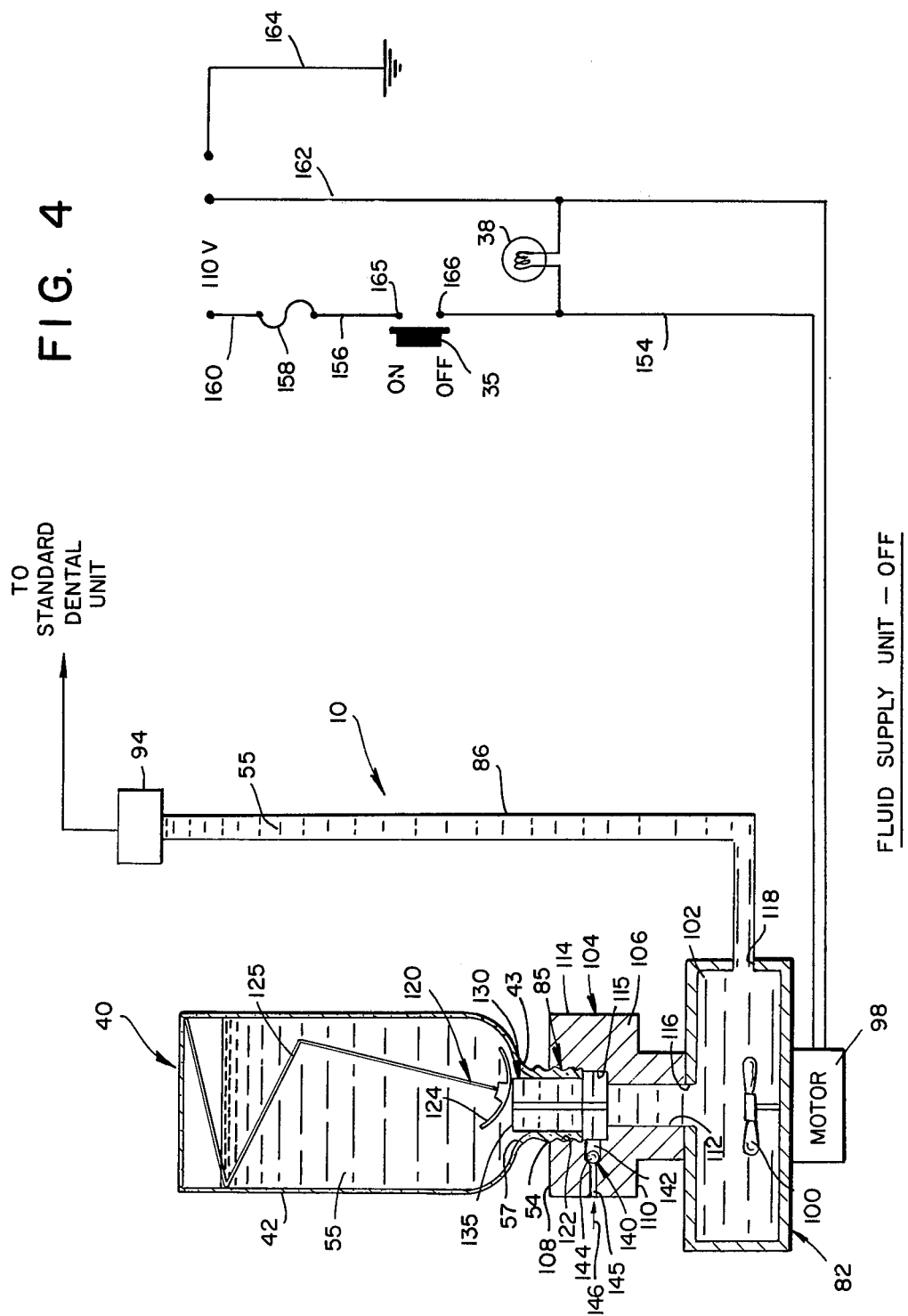

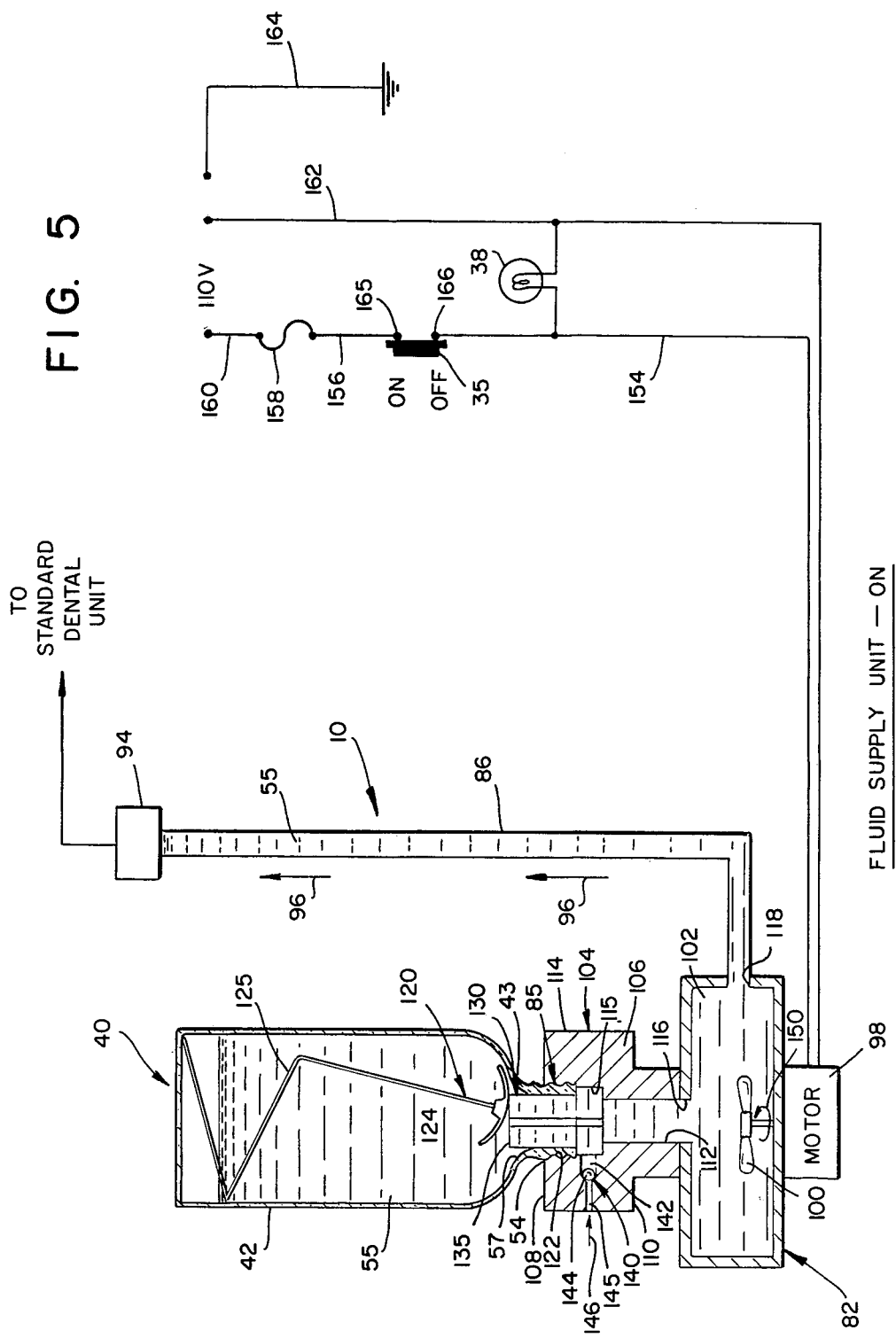

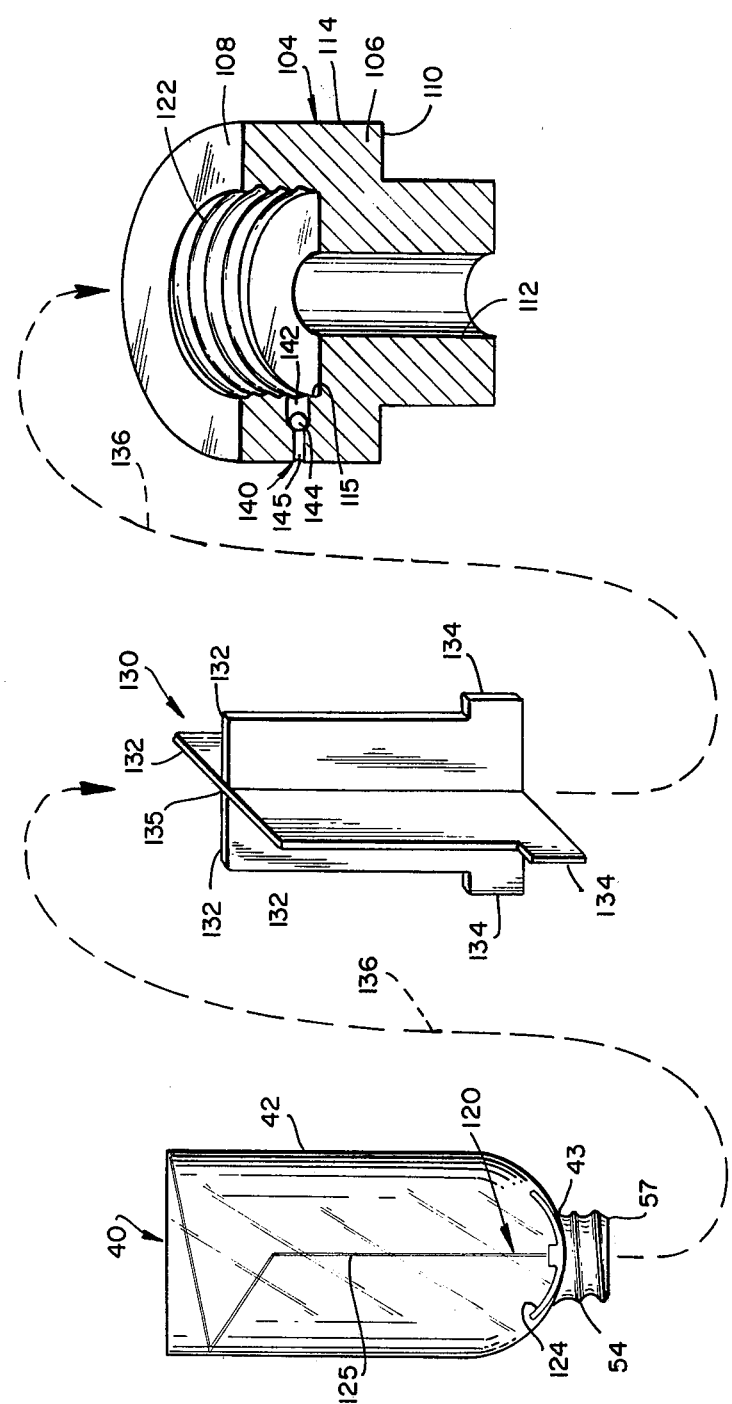

FLUID SUPPLY UNIT — NO BOTTLE or IMPROPERLY POSITIONED

FLUID SUPPLY UNIT — ACCESS DOOR OPEN

FLUID SUPPLY UNIT AND SYSTEMS FOR DENTAL AND MEDICAL INSTRUMENTS

CROSS-REFERENCE TO RELATED APPLICATION

This application is a continuation-in-part of our copending application Ser. No. 702,536, filed July 6, 1976 and now abandoned, which entire subject matter of the copending application is incorporated herein by reference as if fully set forth herein.

BACKGROUND OF THE INVENTION

The present invention relates to a unit adapted to be used in conjunction with conventional professional dental and medical units to perform a variety of functions and procedures with respect to a patient.

The concern of the inventors that tap water should not be utilized by the medical profession has been confirmed in an article entitled "Microbial Contamination of Dental Units and Ultrasonic Scalers", that appeared in the Journal of Periodontology, November 1976. The article clearly states that—"Obviously there is a need for control of bacterial contamination of dental unit water lines either through modification of design or other means that would guarantee the sterility of the water introduced into the patient's mouth". The present invention as well as the co-pending application referred to above provides solutions for the hazards set forth in the article.

Heretofore, except for U.S. Pat. No. 3,924,335 the use of ultrasonic energy in dentistry for professional purposes has been limited to the use of water as the fluid utilized within dental prophylaxis procedures in order to remove foreign substances from within the oral cavity and perform other dental procedures. The present inventors have now discovered that it is possible to adapt conventional ultrasonic prophylaxis, and other dental units presently in use, and being purchased by the dental profession, to have the capacity to deliver selected fluids to the operative site.

Conventional ultrasonic prophylaxis units as manufactured by several companies presently use tap water as the fluid to aid in the dental cleaning process. As the drinking water condition deteriorates, and from time to time in certain cities is undrinkable for periods of time, the dentist with his present equipment has no choice but to continue using tap water in his ultrasonic dental prophylaxis unit.

The number of conventional dental ultrasonic prophylaxis units in use today is believed to approximate 120,000 units on a world wide basis. In addition, annual sales of new units is believed to approximate 20,000 units per year. Many of the new units are purchased by dentists opening their first or a second operatory as well as replacement of older units.

The ability to adapt the units presently in use to pump a fluid selected by the dentist or oral hygienist will permit a savings to the dentist in that only an accessory or auxiliary unit in accordance with this invention need be purchased. Accordingly, by use of the present invention a host of dental procedures not heretofore available may be realized by a system that permits dentists to select fluids having various chemical formulations such that both physical and psychological beneficial results are obtained for their patients. By the provision of the accessory unit of the present invention interchangeable and replaceable fluid supply sources can be directed through the conventional ultrasonic dental handpiece, the scope and variety of dental techniques are increased to a considerable extent.

It might be stated that this additional flexibility given to the dentist permits a number of dental procedures to be carried out that were heretofore not practicable with his conventional equipment.

By the way of background, the use of Kilohertz ultrasonic energy in the dentist's office has become commonplace. At present all of the professional ultrasonic dental units being marketed do not provide an option to the dentist as to a choice of fluid use. The inventors have now discovered that the benefits set forth in the above referenced U.S. Pat. No. 3,924,335 can be obtained with an auxiliary unit so that presently existing units on the market can be easily adapted to give the user a choice of fluid.

The inventors have been involved in the historical growth of these techniques and procedures, and have carefully followed and evaluated the changing requirements which improved dental and medical equipment should embody. In this patent, such novel improved equipment and new techniques are provided for.

The removal of calculus from gingival and subgingival hard tooth surfaces (dentin and enamel) is one of the chief problems facing the periodontist in treating the undesirable conditions found in the mouth, and is essential for maintaining and restoring good dental health. A chemical solution is often used which selectively stains plaque and calculus and thereby assists the dentist in determining the thoroughness of a given prophylactic oral treatment. Such a solution is called a disclosing solution.

OBJECTS OF THE INVENTION

An object of the present invention is to provide an auxiliary fluid supply unit that is adapted to be used in conjunction with commercially available dental and medical equipment.

Another object of the present invention is to provide a fluid supply unit that can be utilized in conjunction standard ultrasonic dental instruments and simultaneously provide selected fluids thereto, without any electrical interconnection.

Another object of the present invention is to provide a novel fluid supply unit that can be readily installed to operate in conjunction with convention dental equipment such that all the fluid used in the dental procedure is sterile.

Other objects and advantages of the invention will be apparent as the disclosure proceeds.

SUMMARY OF THE INVENTION

The present invention includes a fluid supply unit to remotely supply fluid to a conventional ultrasonic prophylaxis, or other dental or medical instruments. The dental instrument may include a generator having a fluid control valve and a handpiece with a tip adapted to be inserted within the oral cavity for simultaneously supplying fluid and electrical energy from the generator to the handpiece for ultrasonically vibrating the tip and providing fluid adjacent the work site.

The fluid supply unit of the present invention includes fluid coupling means adapted for connecting the fluid supply unit to the ultrasonic dental instrument so that fluid is communicated through the fluid control valve to the dental handpiece. Fluid reservoir means is provided to permit the utilization of a variety of fluids for performing oral hygienic procedures with the ultrasonic dental instrument. Dispensing means is operatively associated with the coupling means and the reservoir means, and is comprised of pumping means communicating with the fluid reservoir means for pumping fluid from the reservoir means through the coupling means to the ultrasonic dental instrument.

The dispensing means is placed in an operative condition by a switch that is activated when the user intends to use the dental instrument. The pumping means then starts to pump fluid at a blanking pressure which is below the pressure that the total dental system is capable of sustaining, such that the fluid is continuously pressurized when the fluid supply unit is operational.

Accordingly a self contained dental system for supplying sterile fluids is provided that includes a dental instrument having a handpiece with a tip adapted to be inserted within the oral cavity for supplying the sterile fluid through the handpiece. The dental instrument being operational on a generally intermittent basis by the dentist or dental hygienist.

Fluid supply means for use in conjunction with the dental instrument is provided and has fluid dispensing means with pumping means maintained continuously operational. Fluid reservoir means communicates with the dispensing means to permit the utilization of sterile fluids contained in the reservoir means for performing of oral hygienic procedures in conjunction with the dental instrument. The fluid reservoir means is adapted to receive thereon a container having the sterile fluid therein for dispensing to the dental instrument through the open end of the container. The container includes a closure resiliently mounted in the container normally closing the open end thereof. Opening means is operatively associated with the reservoir means for depressing the closure so as to permit a flow of fluid from the container into the pumping means.

Fluid coupling means is provided for connecting the dispensing means to the dental instrument so that fluid from the reservoir means is communicated to the dental handpiece and dispensed therethrough. The pumping means by being continuously operational maintains the fluid in the coupling means under pressure so as to obtain an immediate flow of fluid to the handpiece upon each occasion that the dental instrument is brought into an operational condition, which may be by a footswitch or fingerswitch.

The dental instrument may be an ultrasonic dental prophylaxis unit, or a rotary drill having interchangeable tips. Other forms of dental and medical instruments may also form part of a system in accordance with the present invention.

The dispensing means includes a cable member adapted to be removably secured to the dental instrument and the dispensing means so as to permit the flow of the fluid through the cable to the dental instrument. In addition mounting means is provided so that the container may be in releasably fixed relationship to the fluid reservoir means.

In accordance with one embodiment of the present invention the pumping means is adapted to pump air for pressurizing the reservoir means. There is provided venting means operatively associated with the pumping means and the dispensing means. The venting means is movable between an open position to vent air supplied by the pumping means to the atmosphere to a closed position so as to cause the air supplied by the pumping means to be supplied to the reservoir means for pressurizing same.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

FIG. 4 is a schematic more or less diagrammatic view of the fluid supply unit illustrated in the "OFF" position;

FIG. 5 is a view similar to FIG. 4 illustrating the fluid supply unit in the "ON" position;

FIG. 6 is an exploded view illustrating one manner in which the fluid container may be removably secured to the fluid supply unit;

DETAILED DESCRIPTION OF THE DRAWINGS

Figure 1:
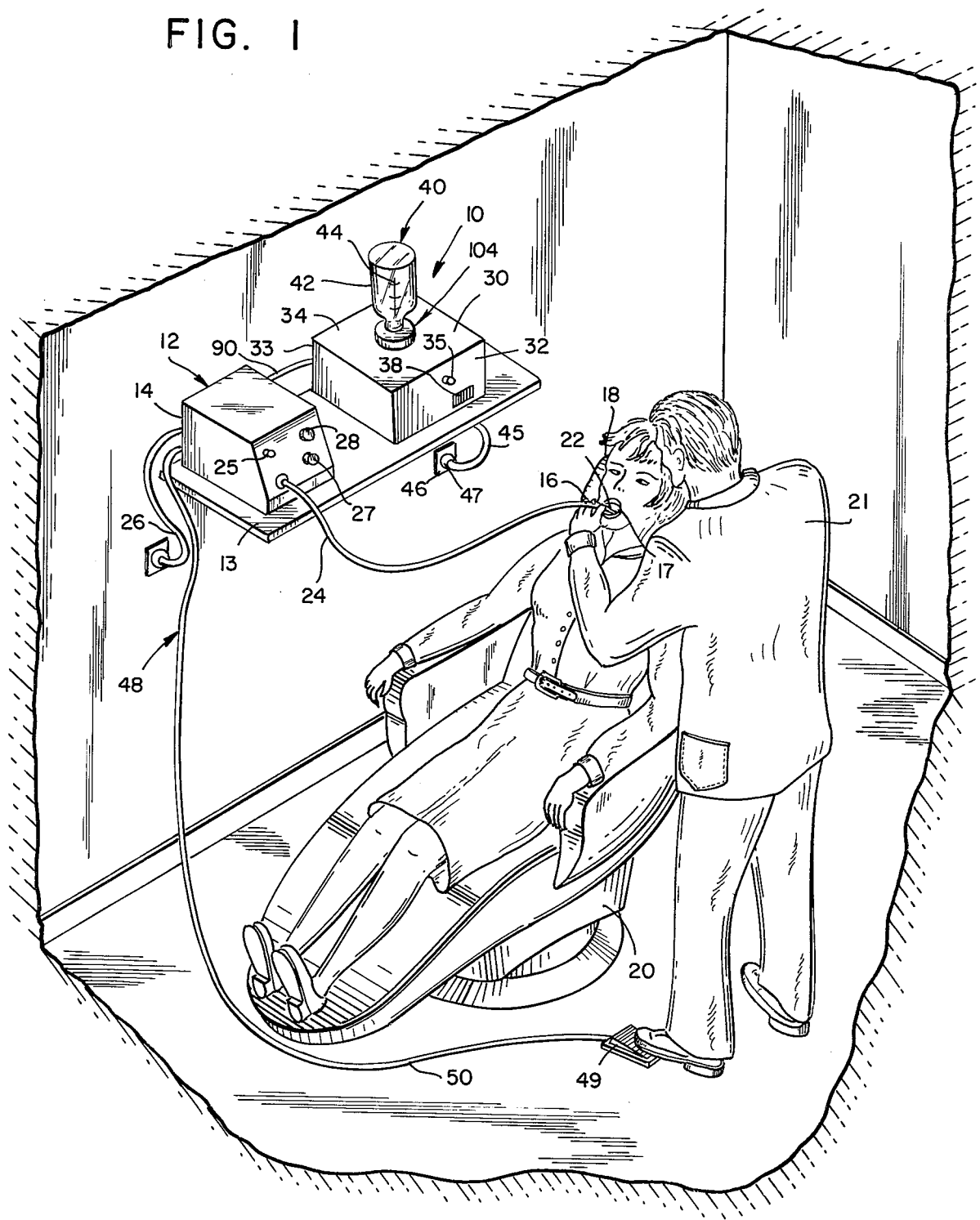
FIG. 1 is a perspective view of the fluid supply unit in operation with one form of dental unit in accordance with the present invention.

Referring now to the drawings, and initially to FIGS. 1 through 6, there is illustrated an auxiliary fluid supply unit 10 that is adapted to be used in conjunction with a variety of commercially available dental and medical instruments. One such instrument or unit 12 that is well known and in use today in dental offices around the world may be in the form of an ultrasonic prophylaxis unit. The fluid supply unit 10 and dental instrument 12, the combination of the two also referred to herein as the ultrasonic fluid supply and dental system, may both be positioned on a table or other support 13 adjacent each other, or spaced from each other up to several or more feet but functioning in unison. The ultrasonic dental prophylaxis instrument 12 is comprised of a generator 14 that may take various forms and shapes, and having a handpiece 16 for use within the oral cavity 17 of a patient 18 that is illustrated in a reclined position on a dental chair 20 being treated by a dentist or other trained person 21.

Figure 2:
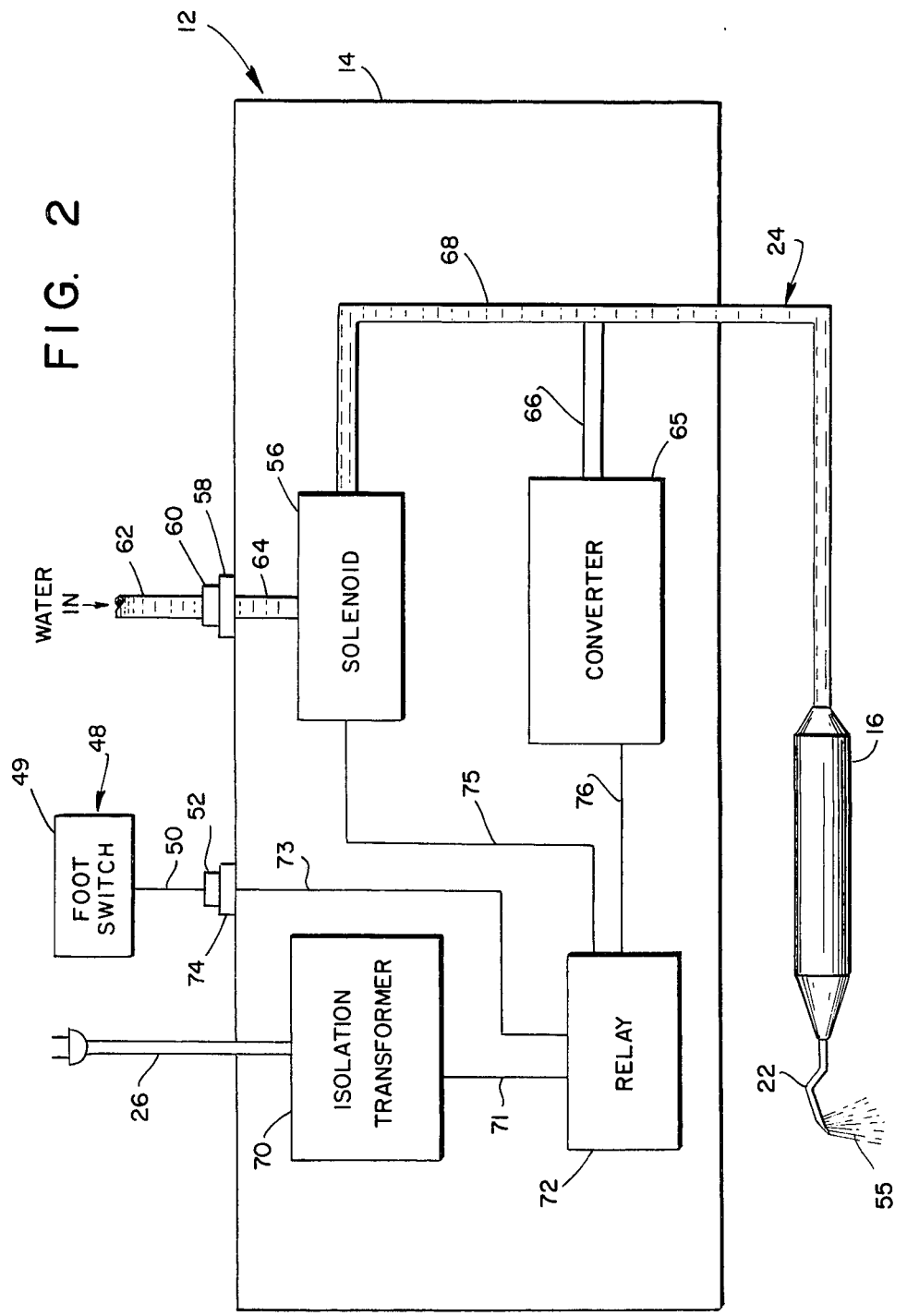
FIG. 2 is a diagrammatic view illustrating the various components of a standard ultrasonic dental prophylaxis unit with which the present invention may be utilized.

The dental instrument 12, as illustrated in FIG. 2, includes a tip 22 extending from one end of the handpiece 16 that is inserted within the oral cavity 17 to perform a variety of functions well known in the art. The generator 14 is contained in a cabinet 15 and is connected to the handpiece 16 by means of cable 24 which carries both the fluid supply lines thereto, as well as the power line to supply the electrical energy to the handpiece 16. The handpiece 16 has an ultrasonic motor contained therein for ultrasonically vibrating the tip 22 and providing fluid adjacent the work site on a command basis as required by the dentist 21.

The dental instrument 14 normally contains a power ON-OFF switch 25 to permit the line current received through the power line cord 26 to energize the dental instrument 12. In addition, the dental instrument 12 normally includes a fluid regulating valve with a handle or knob 27 that is adjustable to regulate the flow of the amount of fluid through the cable 24 and out of the handpiece 16. A fluid control valve mounted in the generator 14 is connected to the fluid regulating valve, and in the open position thereof fluid then flows through the handpiece 16. The dental unit 12 also includes power regulating means having a control knob 28 so that the amplitude of ultrasonic vibration at the tip 22 may be varied. These are the essential features contained in commercially available dental prophylaxis instruments presently on the market.

Prior to the present invention the dentist would normally activate the instrument 12 by means of a footswitch, and the supply of fluid would be ordinary tap water which the inventors believe should be avoided for use in the various dental procedures performed by the dentist. Although the dental instrument 12 has been illustrated to be housed as a separate unit, there are commercially available ultrasonic dental instruments that form part of a console with other non-ultrasonic dental instruments that are presently available and in use in dental offices. The present invention is intended to be used with the ultrasonic dental prophylaxis instrument that is contained in a console as well as the other dental instruments as well. In addition, there are those units in which the dentist has a fingertip switch on the handpiece in lieu of a footswitch and the present invention is adaptable for use with these types of dental and medical instruments as well.

In view of the fact that there is presently in existence tens of thousands of units in dental offices, the fluid supply unit 10 of the present invention was so designed to be compatible for use therewith without the necessity of modifying the existing dental instruments 12 and without having to rework or even enter the generator 14 to make any modifications thereto. This was an important consideration in order to permit quick and easy installation of the auxiliary fluid supply unit 10 in the dental office so that the dentist or even his assistant could place the auxiliary supply unit 10 in operation.

As illustrated in FIG. 1, the fluid supply unit 10 includes housing means 30 which may be in the form of a cabinet having a front panel 32, rear panel 33, and upper surface or wall 34. Certain controls are contained on the front panel 32 and include a power energizing means in the form of a switch 35 having ON and OFF positions, which may include an indicator light 38 thereon so that the user is aware when the switch 35 is in its ON position.

The reservoir means 40 is illustrated as mounted on the cover 34 and may take various shapes and forms, as well as being of various sizes. The fluid reservoir means 40 may be in the form of a transparent or translucent glass or plastic container or bottle 42 having indicia means 44 thereon which may be in the form of calibrated markings to assist the dentist viewing the amount of fluid therein available. To power the fluid supply unit 10, a power cord 45 is plugged into a conventional wall outlet 46 by means of power plug 47.

The operation of the dental instrument 12 may be controlled by the dentist by the utilization of a footswitch assembly 48 that includes a footswitch 49 that is connected by means of footswitch cable 50 to an electrical outlet on the generator cabinet 15.

Referring now to FIGS. 2–6, the diagrammatic and electromechanical operations of the fluid supply unit 10 and dental instrument 12 and the interrelated operational features therebetween are described with respect to these figures. Referring to FIG. 2, there is illustrated the normal functional relationship of the standard dental unit 12, which includes the handpiece 16 with the tip 22 extending from one end thereof and with fluid 55 exiting at or adjacent the tip 22. A variety of either flow-through tips 22 are available, or those in which a fluid outlet tube terminates adjacent the tip 22 are also commercially available, and the equipment of the present invention is adapted for use with both these types as well as with magnetostrictive or piezoelectric motors contained within the handpiece 16.

The generator 14 normally has contained therein a water solenoid or fluid control valve 56 that enters the generator 14 through a fluid coupling adapter 58 that is mounted on the rear wall of the generator cabinet 15. The adapter 58 generally receives and mates with a coupling adapter 60 contained at one end of the fluid conduit or tubing 62. The other end of the conduit 62 normally has an associated coupling member that is connected to the conventional source of water. Within the generator 14 there is an appropriate conduit 64 connecting the fluid adapter 58 to the solenoid 56. The cable assembly 24 is adapted to transmit both the fluid 55 and electrical energy from the converter 65 forming part of the generator 14. An electrical lead 66, shown schematically, is joined to the fluid conduit 68 extending between the solenoid 56 and the handpiece 16.

The power cable 26 is connected to an isolation transformer 70, which in turn is connected electrically by lead 71 to a switch in the form of a relay 72, which in turn is connected by footswitch lead 73 to a receptacle connector or plug 74 mounted on the exterior of the generator 14. The footswitch assembly 48 has the power cord 50 running from the footswitch 49 with the plug 52 adapted to mate with the connector 74. The relay 72 is electrically connected by lead 75 to the solenoid 56, and the relay 72 is also electrically connected by lead 76 to the converter 65.

Under normal operating conditions activation of the footswitch 49 closes the circuit through the relay 72, and the solenoid 56 is brought into an open position permitting fluid from the outside source through conduit 62 to flow therethrough, and simultaneously the converter 65 is activated in order to ultrasonically vibrate the tip 22. The manual fluid control knob 27 on the generator cabinet 15 is coupled to the solenoid 56, in a manner not shown, to regulate the volume of fluid 55 flowing through the unit.

Figure 3:
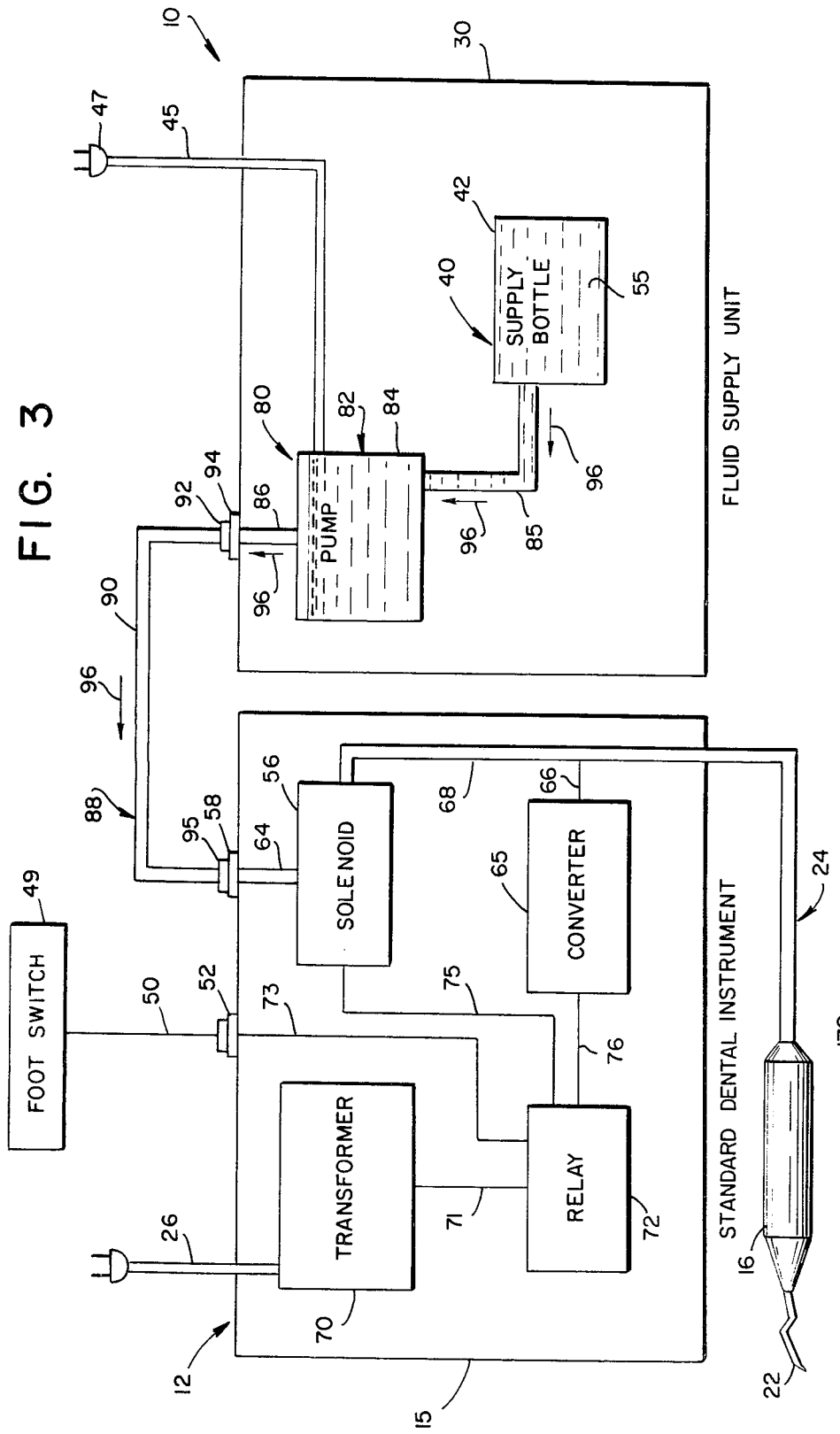
FIG. 3 is a diagrammatic view illustrating the interconnection of the combined standard dental instrument and fluid supply unit, hydraulically coupled together.

Referring now to FIG. 3, the auxiliary fluid supply unit 10 is diagrammatically illustrated as connected with the dental instrument 12. The housing means 30 has either mounted therein or associated therewith various hydraulic components adapted to operate on an interrelated basis with each other and in conjunction with the dental instrument 12 in order to instantaneously provide fluid delivery as required.

Operatively associated with the fluid reservoir means 40 is fluid dispensing means 80 which may include in interconnected fashion pumping means 82, which includes a pump 84 that may take various forms and shapes. The pumping means 82 is connected with the fluid reservoir means 40 by reservoir interconnecting means 85 to permit a continuous flow to be available to the pump 84 from the fluid reservoir container 42.

It has been found that if the pumping means 82 is maintained continuously operational there will be provided in the fluid coupling means 88 a continuous pressure so as to obtain an immediate flow of fluid 55 to the handpiece 16 when the dental unit 12 is energized and the fluid control valve 56 is open. In this manner on each occasion that the dental instrument 12 is operational there will be an immediate flow of fluid to the dental tip 22.

The coupling means 88 is adapted for connecting the fluid dispensing means 80 to the dental instrument 12 so that fluid 55 from the reservoir means 40 is communicated to the dental handpiece 12 and dispensed therethrough. The fluid interconnecting means 88 may include a fluid cable 90 and a fluid connector 92 that is connected to coupling member 94.

The fluid coupling means 88 is such that at one end the fluid conduit 90 may be readily connected by fluid connector 92 to the coupling member 94 which may be part of the housing means 30. The opposite end of the fluid cable 90 may have thereon a fluid connector 95 which in turn is easily joined to the adapter 58. In this manner fluid 55 may flow in the direction of arrow 96 so as to provide a continuous supply to the work site.

FIGS. 4 through 6 illustrate the manner in which the bottle or container 42 of the fluid reservoir means 40 may be mounted for dispensing of the fluid 55 therefrom. As illustrated in FIG. 4 the pumping means 82 may include an externally mounted pump motor 98 having an impeller blade 100 extending within a fluid chamber 102 associated therewith. The reservoir interconnecting means 85 connects the fluid container 42 to the pump 84 of which the motor 98 forms a part thereof.

The container 42 of the fluid reservoir means 40 is designed and adapted to be readily engaged with the dispensing means 80. To provide this ease of assembly the interconnecting means 85 may take various forms and shapes. One such form as illustrated herein includes mounting means 104 adapted to extend at least partially above the housing 30. The mounting means 104 may include a body portion 106 having an upper surface 108 and the bottom surface 110 spaced therefrom. The body portion 106 may have an axially extending bore 112 and an outer surface 114. A seat 115 extends in alignment with the bore 112 to permit fluid flow into the pump cavity 102.

The pumping means 82 has an inlet port 116 and an outlet port 118. The bore 112 mates with the inlet port 116. The container 42 preferably has associated therewith a closure or closing means 120 that is resiliently mounted on the container 42 normally closing one end 43 thereof. The end 43 may have a threaded portion 54 contained thereon. The adapter or body portion 106 for receiving the end 54 of the container 42 may have a threaded portion 122 that is contained in the recess or seat 115 such that the coupling of the container 42 to the adapter 106 is easily accomplished.

In this manner the container 42 is easily changed after the fluid 55 contained therein is dispensed. The closure 120 may be of the form having a head portion 124 that is adapted to extend within the neck 57 of the bottle 42. A spring 125 normally forces the head portion 124 into its sealing or closed position. The interconnecting means 85 further includes opening means 130 associated therewith. The opening means 130 is provided for depressing the closure 120, as illustrated in FIG. 4, so as to permit a flow of fluid 55 from the container 42 into the pumping means 82. As illustrated in FIG. 6 the opening means 130 may include a plurality of arms 132 extending upwardly from a base 134. The base 134 is adapted to be secured within the recess 115 and having an upper end or top 135 that extends above the upper surface 108 of the adapter 106. As illustrated in FIG. 6 by the dotted arrows 136 the interrelationship of the container 42, opening means 130 and mounting means 104 is shown.

It is appreciated that the closure 120 may take various forms, and although the present embodiment illustrates that the closure 120 is contained within the container 42, it may also be of a construction that is mounted externally on the threaded portion 54. The reason for using a closure 120 is to avoid spillage of the fluid 52 as the container 42 is assembled into position. It has also been found that an open well may be utilized to receive the end 43 of the container 42. But in view of the fact that a sterile condition is to be maintained it has been found that a threaded coupling would be preferred, since the fluid 55 has a minimal exposure to the atmosphere.

As the pumping of the fluid continues, and in order to avoid creating a vacuum within the container 42, which is rigid, then air must replace the fluid 52. To accomplish this there is provided venting means 140 operatively associated with the pumping means 82 and the dispensing means 80. One venting arrangement is illustrated in FIGS. 4 and 5 and may include a one way check valve 142 having a valve member 144 mounted therein. An intake opening 145 communicates with the recess 115. From time to time air will flow in the direction of arrow 146 when the sealing member 144 is momentarily depressed inwardly due to pressure fluctations. This movement of closure member 140 permits the air in the atmosphere to enter the system and in turn the container 42. If a thin wall flexible container 42 is used in accordance with this invention, then the venting means 140 would not be required.

The pumping means 82 is connected by the conduit 86 to the coupling member 94, which in turn is connected to the dental unit 12. The conduit 86 is connected to the outlet port 118 of the pumping means 82. The rate of pumping is directed to the size and power of the motor 98 as well as the capacity of the pumping means 82.

The pumping means 82 is selected such that it may run continuously and maintain and create a blanking pressure which is below the pressure that the total dental system comprised of the fluid supply unit 10 and the dental unit 12 can readily sustain. In this manner the fluid 55 is continuously pressurized when the supply means or unit 10 is operational. For an ultrasonic dental application the on cycle may last from a few seconds upward and then there would be an off cycle, followed by an on cycle. Since these cycles may be of rather short time duration it has been found that the start up time of the motor 98 and the rotation of impeller 100, to build up the pressure of the fluid 55 in the respective conduits 86, 90, 64 and 68 was too long a period for most applications. Accordingly, the present invention is such that when the power switch 35 is brought to its on position the motor 98 will continuously rotate the impeller 100 in the direction of arrow 150. What this means is that there is maintained in the pressure lines 86, 90 and 64 the fluid 55 under a "head" of pressure. In this manner immediately upon the control valve 56 being open by the footswitch 49 there will be a flow of fluid 55, since the motor 98 has remained on.

The circuit of the supply unit 10 illustrated in FIGS. 4 and 5 shows that the switch 35 is connected by lead 154 to the motor 98 and by lead 156 to a fuse 158 that is in turn connected by lead 160 to a source of conventional electrical current, such as 110 volts. Lead 162 is in turn connected to motor 98. The indicator light 38 may be connected between leads 154 and 162. Ground lead 164 may be provided. In FIG. 5 the switch 35 has been depressed so as to electrically connect the switch terminals 165 and 166 to each other such that the electrical energy flows therethrough. In this manner the motor 98 remains operational until the switch 35 is brought to its OFF position.

In this manner the user will engage the switch 35 making the supply unit 10 operational prior to, or at about the same time that the power switch 25 on the dental unit is activated. Within a few seconds after activation of the switch 35 the fluid lines are pressurized as discussed above. The dentist or other user of the dental equipment, will then have almost an instantaneous flow of fluid 55 each time the footswitch 49 is so activated. By selecting the pumping means 82 such that the proper blanking pressure is obtained then the system will not leak nor will the motor 98 be affected. What happens is that there is a leak back after a certain pressure is reached, such that although the impeller 100 continues to rotate there is a blanking or upper pressure of the pump that is reached and a system remains at that pressure level.

The supply unit 10 has control means which is formed by the switch means or switch 35 that is electrically connected to the pumping means 82, such that activation of the switch means 35 energizes the pumping means 82. The fluid utilized in the container 42 may be water that is now sterile, or other fluids that may be in the form of a medicament having certain properties desired to be utilized by the dentist. The container 42 which has thereon the indicia means 44 can readily be replaced from time to time as required in a simple manner. In this way the supply unit 10 is easily operated and the fluid supply source is replenished as required.

Figure 3A:
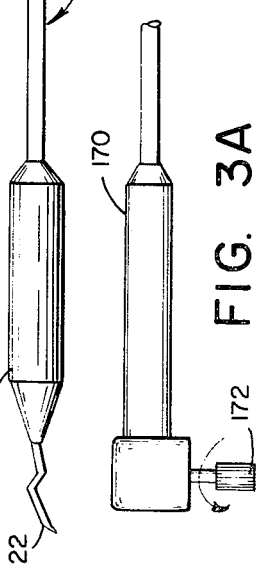
FIG. 3A is a diagrammatic view of another form of instrument, such as a rotary drill used in dentistry, which may be hydraulically coupled to the fluid supply unit of the present invention.
Figure 7:
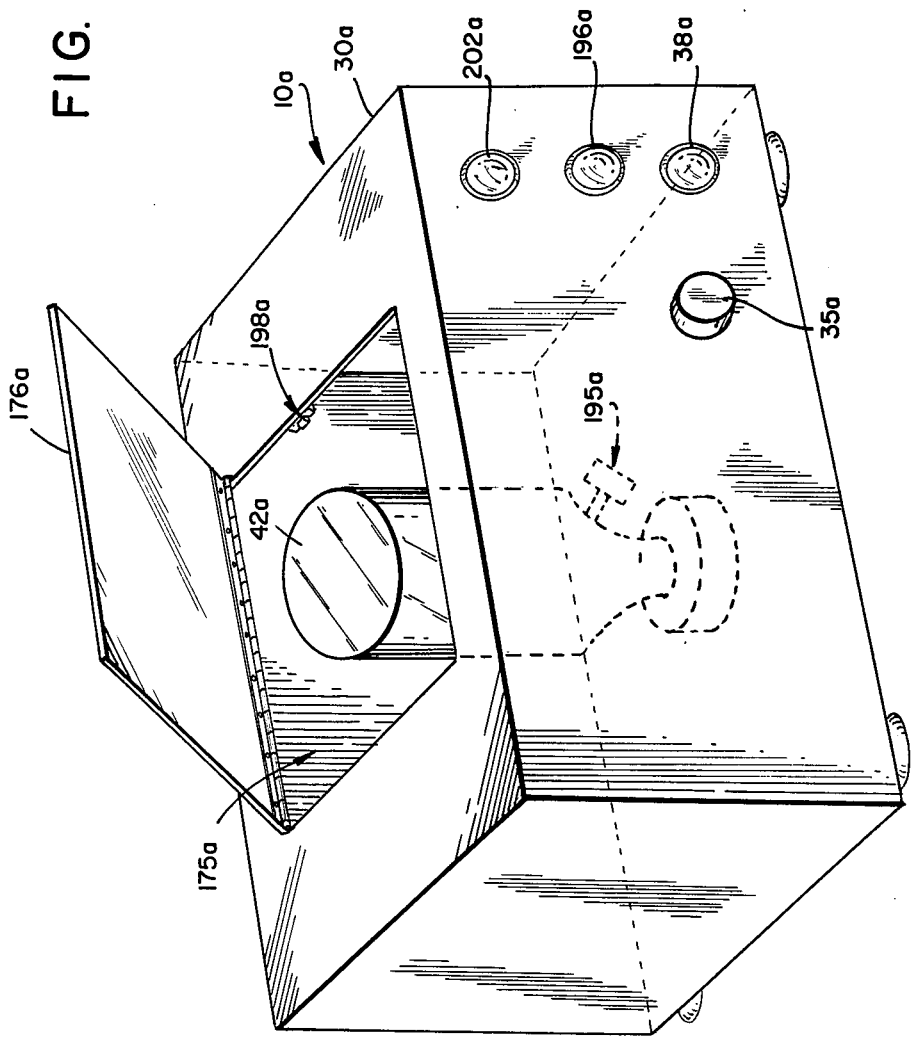
FIG. 7 is a perspective view illustrating an alternate embodiment of the invention in which an air pump is utilized for pumping the fluid.
Figure 8:
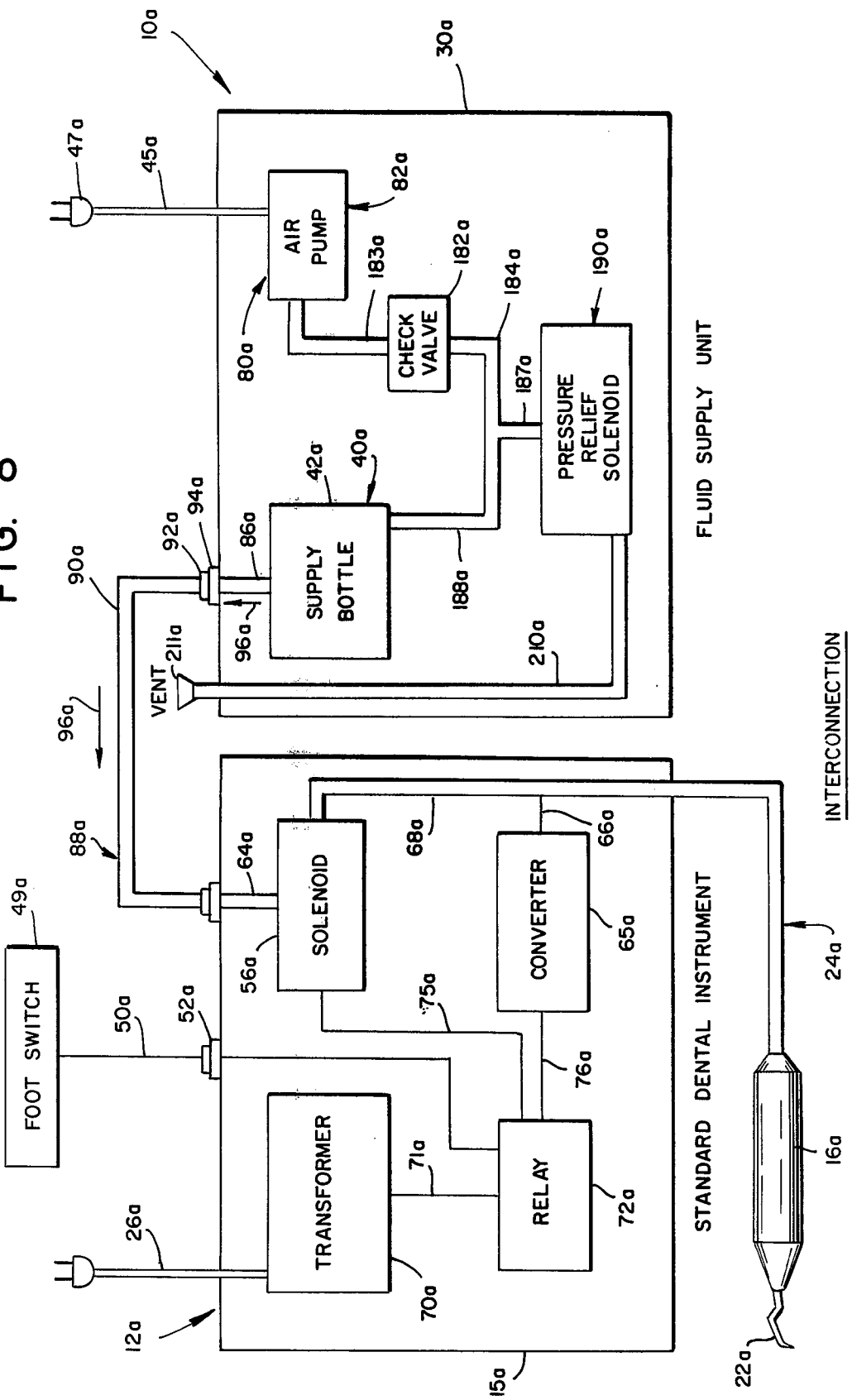
FIG. 8 is a diagrammatic view illustrating the interconnection of the combined standard dental instrument and fluid supply unit, hydraulically coupled together.

It is appreciated that various dental and medical instruments can be easily coupled to the supply unit 10 since there is no electrical interconnection required. One form of dental instrument that may be utilized with the present invention is illustrated in FIG. 3A, which is a rotary drill 170 having a removable tip 172 thereon. The fluid 55 would flow through the drill 170 and exits adjacent the drill tip 172 in a conventional manner. The dental unit may be the complete dental console that is situated in the dental office. There also are other medical devices that require the use of a fluid at the output end thereof that lend themselves for use in conjunction with the present invention.

Referring to FIGS. 7 through 12 there is illustrated another embodiment of a supply unit 10a adapted to supply fluid from the container 42a associated therewith. The supply unit 10a has housing means 30a which may contain therein the pumping means 82a, reservoir means 40a and the fluid coupling means 88a. The housing means 30a having a chamber 175a therein that is adapted to receive the container 42a therein. A door 176a is utilized for enclosing the chamber 175a. In this embodiment the pumping means 82a is adapted to pump air for pressurizing the reservoir means 40a.

The reservoir means 40a includes the container 42a having a closure 120a at one end thereof and the pumping means 82a includes a pair of elements 178a and 179a for opening the closure 120a. One of the elements 178a is adapted for the flow of air into the container 42a to pressurize same with the other of the elements 179a adapted to carry the fluid 52a from the container 42a to the coupling means 88a.

The container 42a may have a cover 180a adapted to receive the elements 178a and 179a as illustrated in FIGS. 9 through 12, which show the sequence of operation of the air pumping means 82a that operates in conjunction with the switch means 35a. The electrical connection is such that lead 160a is connected to fuse 158a which is in turn connected to lead 156a and terminal 165a. Terminal 166a is connected to lead 154a and the air pump 82a. Lead 162a is connected to the air pump in a manner well known in the art. Ground lead 164a may be provided. There may be interposed between the air pump 82a and the container 42a a check valve 182a coupled along conduits 183a and 184a. In this manner the flow of air is only in the direction of arrow 185a.

Upon activation of switch 35a the air pump 82a would continuously remain on and the air illustrated as droplets or air bubbles 186a would continue to enter container 42a to force the fluid 55a therein out through the element 179a and through the conduit 86a to the dental unit 12a. If desired additional features may be provided so as to be assured that the proper functioning between the components of the system 10a takes place. To accomplish this, there is provided between conduit 184a and 188a a pressure relief valve or solenoid 190a. The solenoid valve 190a includes a coil 192a and is connected via wire 193a to lead 162a and via wire 194a to a bottle or container position switch or second switch means 195a.

The container position switch 195a may be mounted within the chamber 175a and depressed automatically when the container 42a is properly positioned in place. An indicator light 196a may be mounted on the housing means 30a to indicate when the switch 195a is in its proper position. As a further safeguard third switch means or a door position switch 198a may be provided and which is automatically depressed when the door 176a is properly closed. An indicator light 202a is electrically connected to the leads 204a and 206a Lead 204a connects switches 195a and 198a to each other. Lead 206a is connected to lead 154a.

Figure 9:
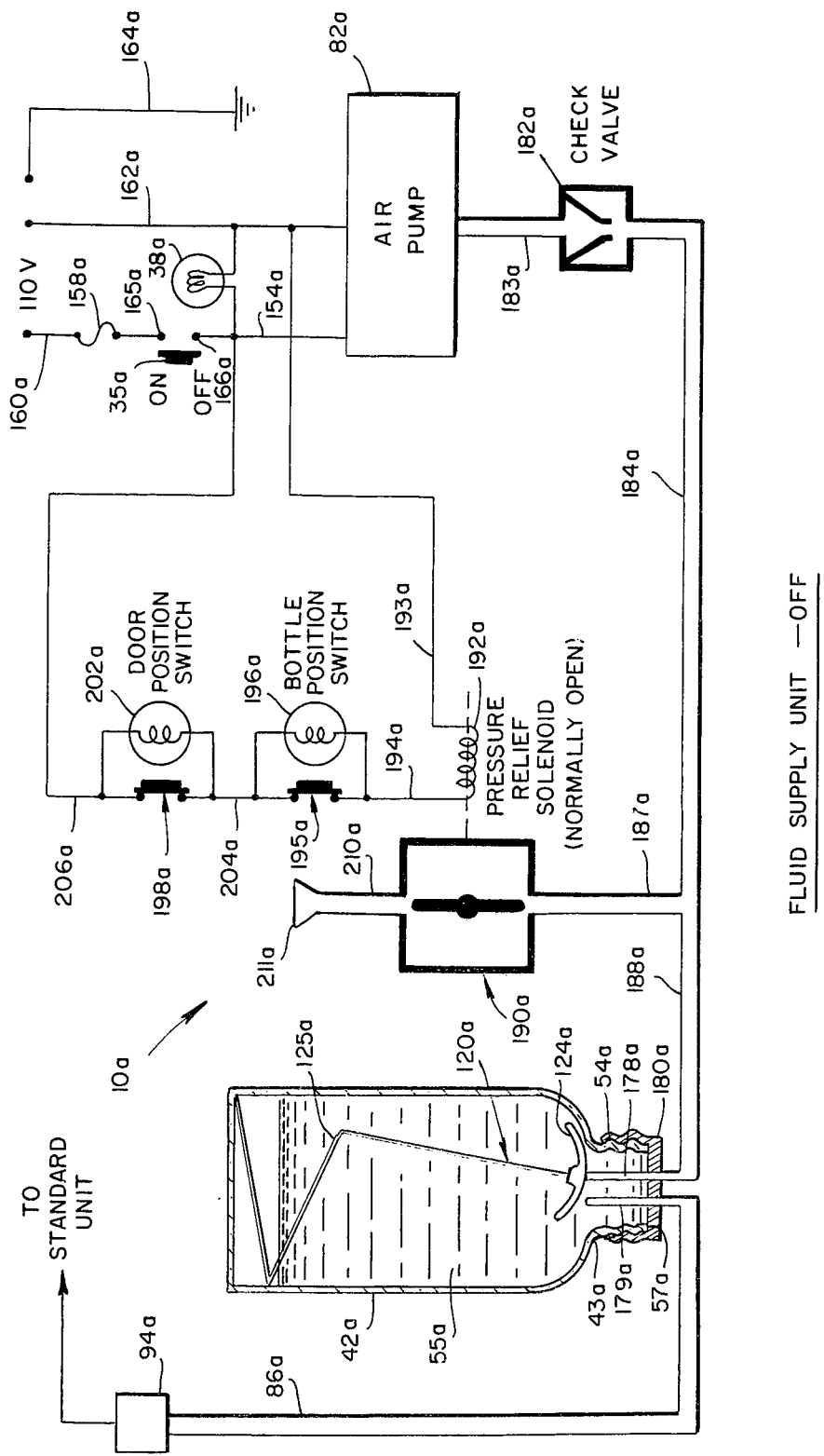
FIG. 9 is a schematic more or less diagrammatic view of the fluid supply unit illustrated in the "OFF" position.
Figure 10:
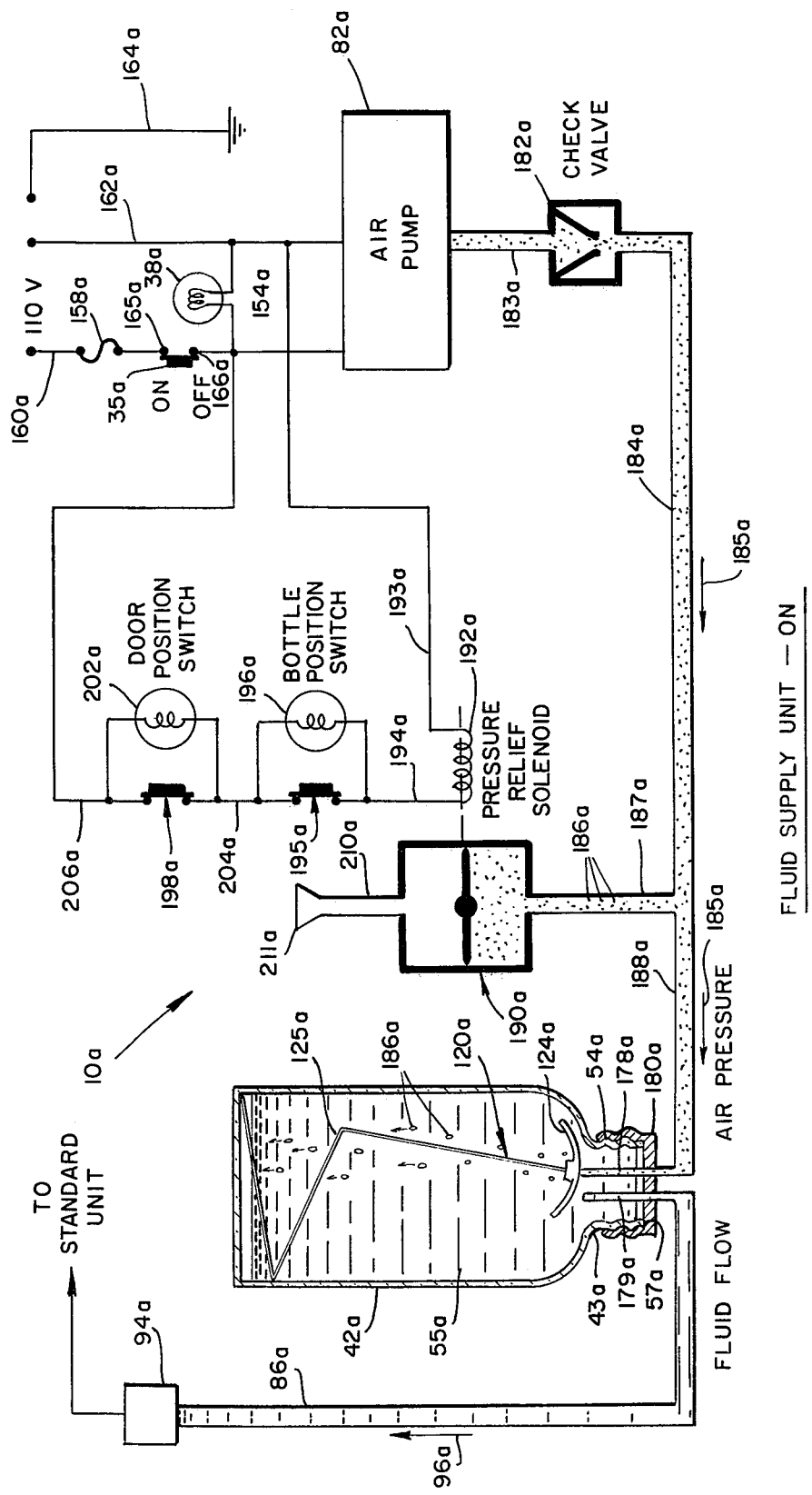
FIG. 10 is a view similar to FIG. 9 illustrating the fluid supply unit in the "ON" position.
Figure 11:
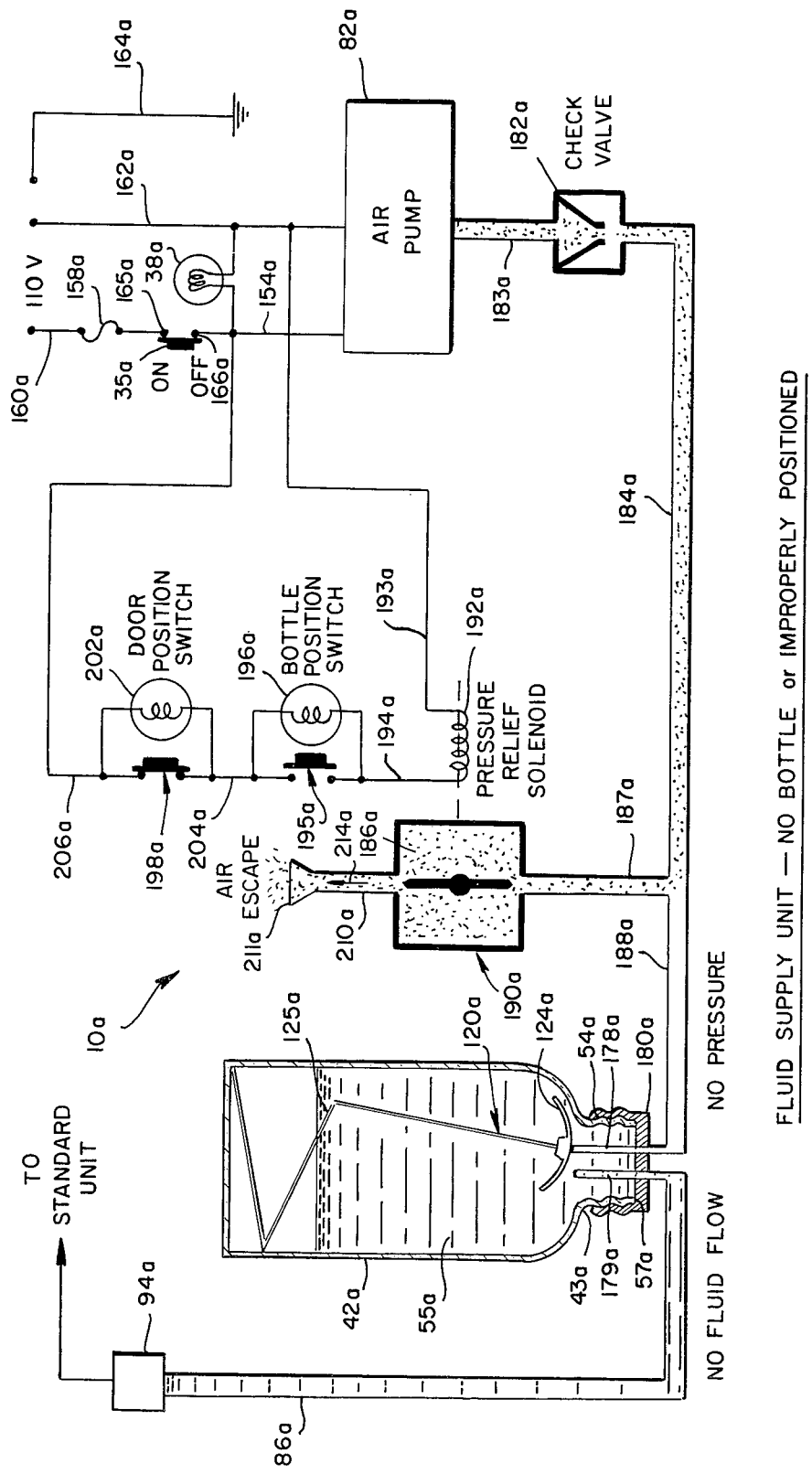
FIG. 11 is a view similar to FIG. 10 illustrating the venting of the supply unit when the bottle or container is improperly positioned or not contained in the unit.

The vent solenoid 190a includes a venting conduit 210a that terminates in a free end 211a. The solenoid 190a is connected by conduit 187a to conduits 184a and 188a. As illustrated in FIG. 9 the supply unit 10a is not in its on position. FIG. 10 illustrates that switch 35a is now in its ON position and that air is being pumped through the system and into the container 42a. If for some reason container 42a is improperly positioned relative to the switch 195a then the pressure relief valve 190a will open and the air 186a will be vented to the atmosphere preventing delivery of fluid 52a to the unit 12a, as illustrated in FIG. 11.

Figure 12:
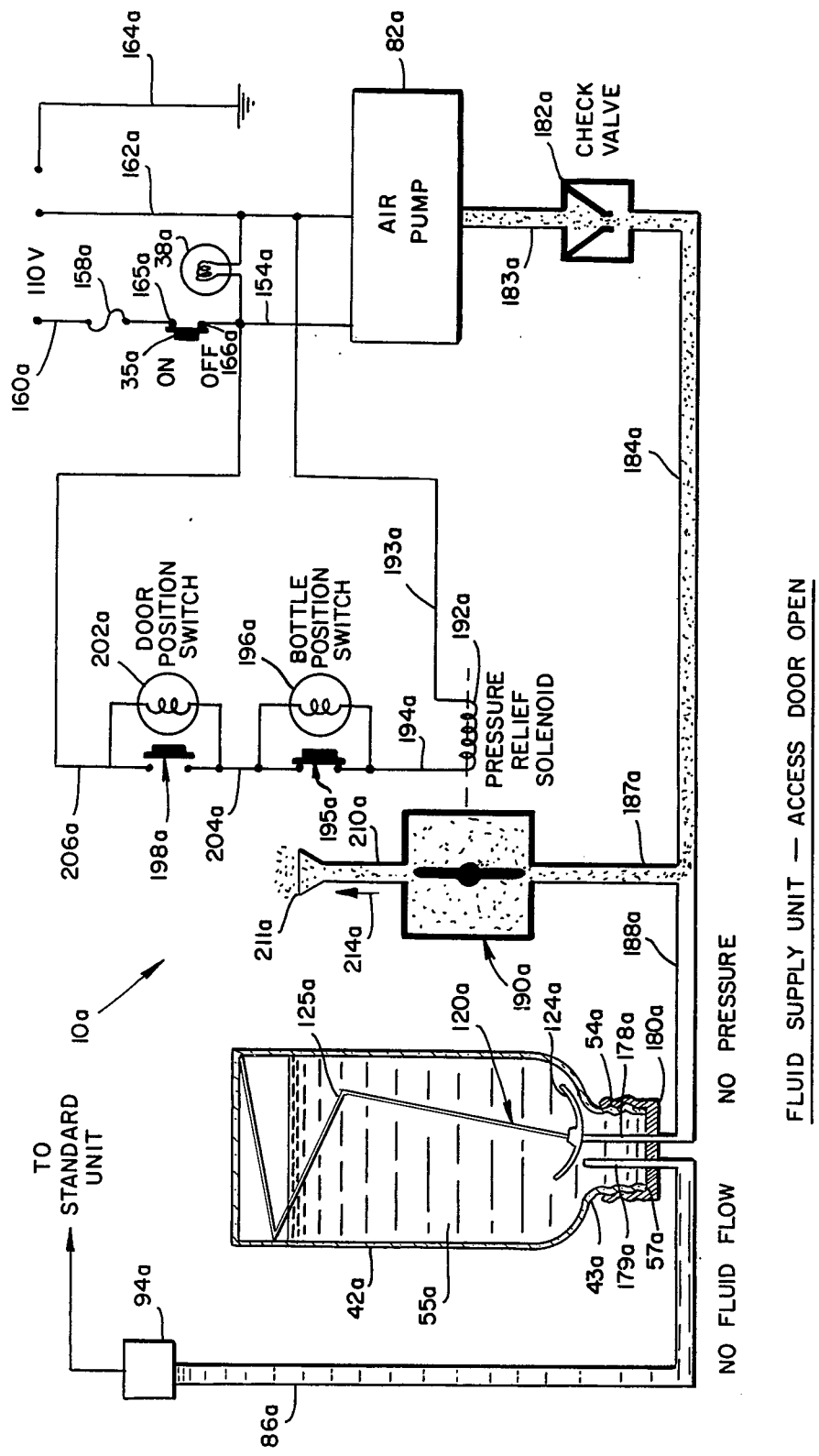
FIG. 12 is a view similar to FIG. 11 but illustrating the venting of the supply unit when the access door is open.

FIG. 12 illustrates the situation in which the door position switch 198a has been left open or has become open. In which case the pressure relief valve 190a will also automatically open and air in the direction of arrow 214a will be vented to the atmosphere. In this manner a simple and safe assembly is provided such that automatic venting can take place if the bottle 42a is improperly positioned in place, or there has been a failure to place a bottle 42a within the chamber 175a.

In all other respects the system 10a operates to maintain a pressure head such that the air pump 82a remains on and there is an immediate flow of fluid 52a to the dental unit 12a as required. At the same time safety provisions are provided in the system 10a. The container 42a would be of a rigid form in order to withstand a pressure build up therein.

Accordingly, the venting means 190a is movable between an open position to vent air supplied by the pumping means 82a to the atmosphere to a closed position so as to cause the air supplied by the pumping means 82a to be supplied to the reservoir means 40a. In this manner the pumping means 82a is adapted to pump air for pressurizing the reservoir means 40a. If desired this air may first be treated or filtered as required.

The container 42a would be replaced as required and the opening means could be the elements 178a and 179a, or a separate opening means may be utilized if desired. It is also appreciated that the supply unit 10a may have associated therewith other means of treating regular tap water such that it becomes substantially sterile. The term "sterile" as used herein means that the fluid is either completely free of or substantially free from living microorganisms. Therefore the water may be treated prior to dispensing through the fluid unit 10a.

It is appreciated that the embodiments of the present invention may be utilized in conjunction with other forms of equipment to obtain the desired sterile levels in the fluid to be dispensed to the patient. These forms of additional equipment may be utilized in conjunction with the present invention.

Although illustrative embodiments of the invention have been described in detail herein with reference to the accompanying drawings, it is to be understood that the invention is not limited to those precise embodiments, and that various changes and modifications may be effected therein without departing from the scope or spirit of the invention, except as defined in the appended claims.

We claim:

1. An enclosed supply unit for use in conjunction with a dental or medical instrument having a handpiece including a tip adapted to be associated within the oral cavity or the like and requiring fluid to be supplied through the handpiece to the tip, said fluid supply unit comprising:
    A. dispensing means for pumping fluid and adapted to be coupled to the instrument so that fluid is supplied to the handpiece,
    B. fluid reservoir means communicating with said dispensing means to permit the utilization of fluids while performing oral hygienic procedures with the instrument,
    C. pumping means operatively associated with said dispensing means, said pumping means being maintained continuously operational to maintain the fluid in said dispensing means under continuous pressure so as to obtain an immediate flow of fluid to the handpiece upon the instrument being operational,
    D. said fluid reservoir means is in the form of a container that is adapted to be readily engaged with said dispensing means and contains a fluid therein for dispensing to the instrument,
    E. mounting means for coupling said container in releasably fixed relationship to said dispensing means, and
    F. venting means operatively associated with said mounting means for venting said container so as to permit a flow of air into said container to replace the fluid displaced therefrom.

2. An enclosed fluid supply unit as in claim 1, wherein
    a. said pumping means communicates with said reservoir means for pumping fluid under pressure to the instrument, and
    b. said pumping means creates a pressure which is below the pressure that the supply unit is capable of sustaining, such that the fluid in said supply unit is pressurized when the supply unit is operational.

3. An enclosed fluid supply unit as in claim 1, wherein said reservoir means includes a container with a closure resiliently mounted on said container normally closing one end thereof.

4. An enclosed fluid supply unit as in claim 3, and further including opening means operatively associated with the supply unit for depressing said closure so as to permit a flow of fluid from said container into said pumping means.

5. An enclosed fluid supply unit as in claim 1, wherein said instrument is an ultrasonic dental prophylaxis unit.

6. An enclosed fluid supply unit as in claim 1, wherein said instrument is a rotary drill having interchangable tips.

7. An enclosed fluid supply unit as in claim 1, and further including control means comprising switch means electrically connected to said pumping means such that activation of said switch means energizes said pumping means.

8. An enclosed fluid supply unit as in claim 1, wherein said pumping means includes a fluid pump having a chamber therein with spaced apart ports connected to said reservoir means and said dispensing means.

9. An enclosed fluid supply unit for use in conjunction with a dental or medical instrument having a handpiece including a tip adapted to be associated within the oral cavity or the like and requiring fluid to be supplied through the handpiece to the tip, said fluid supply unit comprising:
    A. dispensing means for pumping fluid and adapted to be coupled to the instrument so that fluid is supplied to the handpiece,
    B. fluid reservoir means communicating with said dispensing means to permit the utilization of fluids while performing oral hygienic procedures with the instrument,
    C. pumping means operatively associated with said dispensing means, said pumping means being maintained continuously operational to maintain the fluid in said dispensing means under continuous pressure so as to obtain an immediate flow of fluid to the handpiece upon the instrument being operational, D. said fluid reservoir means is adapted to be readily engaged with said dispensing means and contains a fluid therein for dispensing to the instrument, E. said reservoir means includes a container with a closure resiliently mounted on said container normally closing one end thereof, F. said fluid reservoir means includes an adapter for receiving said one end of said container therein, and G. said adapter having a recess for receiving a supply of fluid therein from said container that may be sequentially released as the instrument is operational.

10. An enclosed fluid supply unit for use in conjunction with a dental or medical instrument having a handpiece including a tip adapted to be associated within the oral cavity or the like and requiring fluid to be supplied through the handpiece to the tip, said fluid supply unit comprising:

A. dispensing means for pumping fluid and adapted to be coupled to the instrument so that fluid is supplied to the handpiece, B. fluid reservoir means communicating with said dispensing means to permit the utilization of fluids while performing oral hygienic procedures with the instrument, C. pumping means operatively associated with said dispensing means, said pumping means being maintained continuously operational to maintain the fluid in said dispensing means under continuous pressure so as to obtain an immediate flow of fluid to the handpiece upon the instrument being operational, D. said pumping means being adapted to pump air for pressurizing said reservoir means, E. venting means operatively associated with said pumping means and said dispensing means, said venting means movable between an open position to vent air supplied by said pumping means to the atmosphere to a closed position so as to cause the air supplied by said pumping means to be supplied to said reservoir means, F. said reservoir means includes a rigid container, and G. said pumping means includes a pair of elements for extending within one end of said container, one of said elements adapted for the flow of air into said container to pressurize same with the other of said elements adapted to carry the fluid from said container to the instrument.

11. An auxiliary enclosed fluid supply unit for use in conjunction with a dental instrument having a handpiece with a tip adapted to be inserted within the oral cavity and simultaneously supplying fluid through the handpiece, the dental instrument being operational on a generally intermittent basis, said fluid supply unit comprising:

A. fluid dispensing means having pumping means adapted to be maintained continuously operational, B. fluid reservoir means communicating with said dispensing means to permit the utilization of fluids contained in said reservoir means for performing of oral hygienic procedures in conjunction with the dental instrument, C. fluid coupling means adapted for connecting said fluid dispensing means to the dental instrument so that fluid from said fluid reservoir means is in communicating relationship to the dental handpiece for dispensing therethrough, D. said pumping means when operational maintaining the fluid in said coupling means under continuous pressure so as to obtain an immediate flow of fluid to the dental instrument for dispensing through the handpiece, E. said fluid reservoir means is in the form of a container that is adapted to be readily engaged with said dispensing means and contains a fluid therein for dispensing to the instrument, F. mounting means for coupling said container in releasably fixed relationship to said dispensing means, G. venting means operatively associated with said mounting means for venting said container so as to permit a flow of air into said container to replace the fluid displaced therefrom, H. said pumping means communicates with said reservoir means for pumping fluid under pressure to the instrument, I. said pumping means creates a pressure which is below the pressure that the supply unit is capable of sustaining such that the fluid in said supply unit is pressurized when the supply unit is operational, J. said mounting means includes an adapter for receiving said one end of said container therein, and K. said adapter having a recess for receiving a supply of fluid therein from said container that may be sequentially released as the instrument is operational.

12. A auxiliary enclosed fluid supply unit for use in conjunction with a dental instrument having a handpiece with a tip adapted to be inserted within the oral cavity and simultaneously supplying fluid through the handpiece, the dental instrument being operational on a generally intermittent basis, said fluid supply unit comprising:

A. fluid dispensing means having pumping means adapted to be maintained continuously operational, B. fluid reservoir means communicating with said dispensing means to permit the utilization of fluids contained in said reservoir means for performing of oral hygienic procedures in conjunction with the dental instrument, C. fluid coupling means adapted for connecting said fluid dispensing means to the dental instrument so that fluid from said fluid reservoir means is in communicating relationship to the dental handpiece for dispensing therethrough, D. said pumping means when operational maintaining the fluid in said coupling means under continuous pressure so as to obtain an intermediate flow of fluid to the dental instrument for dispensing through the handpiece, E. said pumping means is adapted to pump air for pressurizing said reservoir means, F. housing means having said dispensing means, pumping means, reservoir means, and said coupling means operatively associated therewith, G. said housing means having a chamber adapted to receive said container therein, H. said housing means having a door enclosing said chamber, and I. said reservoir means includes a container having a closure at one end thereof and said pumping means includes a pair of elements for opening said closure, one of said elements adapted for the flow of air into said container to pressurize same with the other of said elements adapted to carry the fluid from said container to said coupling means.

13. An enclosed fluid supply unit as in claim 12, wherein
   a. said container having one end adapted to be secured to said dispensing means, and
   b. said pumping means pressurizes said container so as to obtain a flow of fluid from said container to the dental handpiece.

14. An auxiliary enclosed fluid supply unit for use in conjunction with a dental instrument having a handpiece with a tip adapted to be inserted within the oral cavity and simultaneously supplying fluid through the handpiece, the dental instrument being operational on a generally intermittent basis, said fluid supply unit comprising:
   A. fluid dispensing means having pumping means adapted to be maintained continuously operational,
   B. fluid reservoir means communicating with said dispensing means to permit the utilization of fluids contained in said reservoir means for performing of oral hygienic procedures in conjunction with the dental instrument,
   C. fluid coupling means adapted for connecting said fluid dispensing means to the dental instrument so that fluid from said fluid reservoir means is in communicating relationship to the dental handpiece for dispensing therethrough,
   D. said pumping means when operational maintaining the fluid in said coupling means under continuous pressure so as to obtain an immediate flow of fluid to the dental instrument for dispensing through the handpiece,
   E. said reservoir means includes a container having a closure at one end thereof and said pumping means includes a pair of elements for opening said closure, one of said elements adapted for the flow of air into said container to pressurize same with the other of said elements adapted to carry the fluid from said container to said coupling means,
   F. control means comprising:
      (1) first switch means electrically connected to said pumping means such that activation of said switch means energizes said pumping means, and
      (2) second switch means operatively connected to said container to automatically vent said pumping means if said container is improperly positioned relative to said reservoir means.

15. An auxiliary enclosed fluid supply unit for use in conjunction with a dental instrument having a handpiece with a tip adapted to be inserted within the oral cavity and simultaneously supplying fluid through the handpiece, the dental instrument being operational on a generally intermittent basis, said fluid supply unit comprising:
   A. fluid dispensing means having pumping means adapted to be maintained continuously operational,
   B. fluid reservoir means communicating with said dispensing means to permit the utilization of fluids contained in said reservoir means for performing of oral hygienic procedures in conjunction with the dental instrument,
   C. fluid coupling means adapted for connecting said fluid dispensing means to the dental instrument so that fluid from said fluid reservoir means is in communicating relationship to the dental handpiece for dispensing therethrough,
   D. said pumping means when operational maintaining the fluid in said coupling means under continuous pressure so as to obtain an immediate flow of fluid to the dental instrument for dispensing through the handpiece,
   E. said fluid reservoir means is adapted to receive thereon a container having the fluid therein for dispensing to the dental instrument through the open end of said container, said container including a closure resiliently mounted on said container normally closing said open end, and
   F. opening means operatively associated with said reservoir means for depressing said closure so as to permit a flow of fluid from said container into said pumping means.

16. An auxiliary enclosed fluid supply unit for use in conjunction with a dental instrument having a handpiece with a tip adapted to be inserted within the oral cavity and simultaneously supplying fluid through the handpiece, the dental instrument being operational on a generally intermittent basis, said fluid supply unit comprising:
   A. fluid dispensing means having pumping means adapted to be maintained continuously operational,
   B. fluid reservoir means communicating with said dispensing means to permit the utilization of fluids contained in said reservoir means for performing of oral hygienic procedures in conjunction with the dental instrument,
   C. fluid coupling means adapted for connecting said fluid dispensing means to the dental instrument so that fluid from said fluid reservoir means is in communicating relationship to the dental handpiece for dispensing therethrough,
   D. said pumping means when operational maintaining the fluid in said coupling means under continuous pressure so as to obtain an immediate flow of fluid to the dental instrument for dispensing through the handpiece,
   E. said fluid reservoir means is adapted to receive thereon a container having the fluid therein for dispensing to the dental instrument through the open end of said container, said container including a closure resiliently mounted on said container normally closing said open end,
   F. opening means operatively associated with said reservoir means for depressing said closure so as to permit a flow of fluid from said container into said pumping means, and
   G. means for mounting said container in releasably fixed relationship to said reservoir means.

17. An auxiliary enclosed fluid supply unit for use in conjunction with a dental instrument having a handpiece with a tip adapted to be inserted within the oral cavity and supplying fluid through the handpiece, the dental instrument being operational on a generally intermittent basis, said fluid supply unit comprising:
   A. fluid dispensing means having pumping means maintained continuously operational,
   B. fluid reservoir means communicating with said dispensing means to permit the utilization of fluids contained in said reservoir means for performing of oral hygienic procedures in conjunction with the dental instrument,
   C. said fluid reservoir means adapted to receive thereon a container having the fluid therein for dispensing to the dental instrument through the open end of said container, said container including a closure resiliently mounted on said container normally closing said open end, D. opening means operatively associated with said reservoir means for depressing said closure so as to permit a flow of fluid from said container into said pumping means, E. fluid coupling means adapted for connecting said fluid dispensing means to the dental instrument so that fluid from said fluid reservoir means is communicated to the dental handpiece and dispensed therethrough, F. said pumping means by being continuously operational maintains the fluid in said coupling means under pressure so as to obtain an immediate flow of fluid to the handpiece upon each occasion that the dental instrument is operational, G. said opening means includes an element for engaging said closure and opening same, H. said dispensing means includes a hose member adapted to be removably secured to the dental instrument and said dispensing means so as to permit the flow of said fluid through said hose member to the dental instrument, and I. means for mounting said container in releasably fixed relationship to said fluid reservoir means.

18. An enclosed fluid supply unit as in claim 17, wherein said dental instrument is an ultrasonic dental prophylaxis unit.

19. An enclosed fluid supply unit for use in conjunction with a dental instrument having a handpiece with a tip adapted to be inserted within the oral cavity and simultaneously supplying fluid through the handpiece, the dental instrument being operational on a generally intermittent basis, said fluid supply unit comprising:

A. fluid dispensing means including pumping means being maintained continuously operational, B. fluid reservoir means adapted to be readily engaged and interchangeable with said fluid dispensing means and communicating with said pumping means to permit the utilization of a variety of fluids for performing oral hygienic procedures with the dental instrument, said pumping means adapted to pump air into said reservoir means for pressurizing same, C. said reservoir means comprising a container having an open end and said pumping means comprising a pair of elements for extending within said open end of said container, one of said elements adapted for the flow of air into said container to pressure same with the other of said elements adapted to carry the fluid from said container, D. fluid coupling means adapted for connecting said fluid carrying element from said container to the dental instrument so that fluid from said fluid dispensing means is communicated to the dental handpiece, E. said pumping means maintaining the fluid in said coupling means under continuous pressure so as to obtain an immediate flow of fluid to the handpiece upon the dental instrument being operational, and F. control means comprising:

(1) first switch means electrically connected to said pumping means such that activation of said switch means energizes said pumping means, and (2) second switch means operatively connected to said container to automatically vent said pumping means if said container is improperly positioned relative to said reservoir means.

20. A self contained dental system for supplying sterile fluids comprising in combination:

A. a dental instrument having a handpiece with a tip adapted to be inserted within the oral cavity for supplying said sterile fluid through the handpiece, said dental instrument being operational on a generally intermittent basis, B. fluid supply means for use in conjunction with said dental instrument, said fluid supply means comprising (1) fluid dispensing means having pumping means maintained continuously operational, (2) fluid reservoir means communicating with said dispensing means to permit the utilization of sterile fluids contained in said reservoir means for performing of oral hygienic procedures in conjunction with said dental instrument, (3) said fluid reservoir means adapted to receive thereon a container having the fluid therein for dispensing to said dental instrument through the open end of said container, said container including a closure resiliently mounted on said container normally closing said open end, (4) opening means operatively associated with said reservoir means for depressing said closure so as to permit a flow of fluid from said container into said pumping means, (5) fluid coupling means adapted for connecting said dispensing means to said dental instrument so that fluid from said reservoir means is communicated to said dental handpiece and dispensed therethrough, and (6) said pumping means by being continuously operational maintains the fluid in said coupling means under presusre so as to obtain an immediate flow of fluid to said handpiece upon each occasion that said dental instrument is operational.

21. A dental system as in claim 20, wherein said dental instrument is an ultrasonic dental prophylaxis unit.

22. A dental system as in claim 20, wherein said dental instrument is a rotary drill having interchangeable tips.

23. A dental system as in claim 20, wherein said fluid reservoir means is vented to the atmosphere so as to permit air to replace the dispensed fluid from said container.

24. A dental system as in claim 20, wherein said dispensing means includes a cable member adapted to be removably secured to said dental instrument and said dispensing means so as to permit the flow of said fluid through said cable to said dental instrument.

25. A dental system as in claim 20, and further including means for mounting said container in releasably fixed relationship to said fluid reservoir means.

26. A dental system as in claim 20, wherein said pumping means is adapted to pump air for pressurizing said reservoir means.

27. A dental system as in claim 26, and further including venting means operatively associated with said pumping means and said dispensing means, said venting means movable between an open position to vent air supplied by said pumping means to the atmosphere to a closed position so as to cause the air supplied by the pumping means to be supplied to said reservoir means.

28. A dental system as in claim 20, wherein said pumping means creates a blanking pressure which is below the pressure that the total dental system is capable of sustaining, such that the fluid is continuously pressurized when said supply means is operational.

29. The method of supplying a selected fluid for dental and medical usages, comprising the steps of:
   A. providing an instrument having a handpiece with a tip adapted to be inserted at the work site for supplying said selected fluid through the handpiece, said instrument being operational on a generally intermittent basis,
   B. coupling fluid supply means to said handpiece for use in conjunction with said instrument,
   C. securing fluid reservoir means in operational relationship with said fluid supply means to permit the utilization of said selected fluid contained in said reservoir means for performing of procedures in conjunction with said instrument,
   D. continuously pumping said fluid from said reservoir means to said instrument so as to create and maintain a pressure which is below the pressure that said instrument is capable of sustaining, such that said selected fluid is maintained at a pressurized level, whereby an intermediate flow of said fluid to said handpiece is obtained upon each said intermittent occasion that said instrument becomes operational,
   E. venting said reservoir means to the atmosphere so as to permit air to replace said fluid dispensed therefrom, and
   F. releasably mounting a container on said fluid reservoir means having said fluid therein.

30. The method as in claim 29, wherein said instrument is an ultrasonic dental prophylaxis unit.

31. The method as in claim 29, wherein said instrument is a dental rotary drill having interchangeable tips.

* * * * *